United States Patent
Kaneda et al.

(10) Patent No.: US 6,952,098 B2
(45) Date of Patent: Oct. 4, 2005

(54) METHOD OF EVALUATING GREEN MALT QUALITIES BY ELECTRON SPIN RESONANCE SPECTROMETRY AND METHOD OF EVALUATING MALT QUALITIES

(75) Inventors: Hirotaka Kaneda, Shizuoka (JP); Kiyoshi Takoi, Shizuoka (JP); Naoko Nishita, Tokyo (JP); Junko Yoshimura, Tokyo (JP)

(73) Assignee: Sapporo Breweries Ltd., Tokyo (JP)

(*) Notice: Subject to any disclaimer, the term of this patent is extended or adjusted under 35 U.S.C. 154(b) by 0 days.

(21) Appl. No.: 10/466,778
(22) PCT Filed: Dec. 3, 2002
(86) PCT No.: PCT/JP02/12678

§ 371 (c)(1),
(2), (4) Date: Aug. 4, 2003

(87) PCT Pub. No.: WO03/048798
PCT Pub. Date: Jun. 12, 2003

(65) Prior Publication Data
US 2004/0066196 A1 Apr. 8, 2004

(30) Foreign Application Priority Data
Dec. 4, 2001 (JP) .................... 2001-370632

(51) Int. Cl.[7] .................................. G01V 3/00
(52) U.S. Cl. ...................................... 324/316
(58) Field of Search ................... 324/307, 309, 324/316

(56) References Cited
U.S. PATENT DOCUMENTS 4,487,766 A * 12/1984 Mach .................. 514/22
5,343,150 A * 8/1994 Nakahata et al. ........... 324/316
5,431,901 A * 7/1995 Halpern et al. ............. 424/9.33
5,811,305 A    9/1998 Ono et al.
6,462,546 B1 * 10/2002 Schmalbein et al. ........ 324/316
6,830,741 B1 * 12/2004 Sakatani et al. ............ 423/610

FOREIGN PATENT DOCUMENTS

WO    98/53042    11/1998

OTHER PUBLICATIONS

H. Kaneda et al.: "The role of free radicals in beer oxidation" J. Am. Soc. Brew. Chem., vol. 47, No. 2, pp. 49–53 1989.

* cited by examiner

Primary Examiner—Diego Gutierrez
Assistant Examiner—Dixomara Vargas
(74) Attorney, Agent, or Firm—Oblon, Spivak, McClelland, Maier & Neustadt, P.C.

(57) ABSTRACT

A method is provided in which a correlation is made between a parameter indicating modification of a sampled malt in a germination process in which barley is germinated, and an ESR signal intensity of the sampled malt. The parameter is determined, in advance, by general analytical methods including chemical analytical methods. The ESR signal intensity is determined by measuring a peak height of spectrum of the sampled malt at a g value at which an unpaired electron derived from a carbon radical is resonant. The ESR signal intensity is a ratio of the measured peak height of spectrum to a peak height of spectrum of a reference, per a unit weight of the sampled malt. The modification state of the sampled malt can be evaluated based on the ESR signal intensity determined by electron spin resonance spectrometry. Kohlbach index, Hartong index at 45° C., diastatic power, β-glucan content, viscosity, and friability may be used as the parameter.

4 Claims, 5 Drawing Sheets

METHOD OF EVALUATING GREEN MALT QUALITIES BY ELECTRON SPIN RESONANCE SPECTROMETRY AND METHOD OF EVALUATING MALT QUALITIES

TECHNICAL FIELD

The present invention generally relates to a quality evaluation method of malt to be used in the production of malt alcoholic beverages such as beer, and, more particularly, to a quality evaluation method of malt using Electron Spin Resonance (ESR) analysis.

BACKGROUND ART

Beer is mainly made of barley malt that serves as the source of starch and enzyme. The production process of beer is classified into a malting process, a brewing process, and a packaging process. In the malting process, malt is steeped into water for germination. During germination, degradative enzymes are activated. The germinating barley is called green malt. After germinating to an expected extent of modification, green malt is dried (kilned). In the next brewing process, water is added to ground malt and is heated for saccharification, and then, is filtered. The filtered liquid is boiled after adding hop, and saccharified liquid (wort) is obtained by separating hop dreg. After cooling, the wort is fermented by adding yeast, and is stored at a cold temperature. After carbon dioxide generated during the storage is dissolved into the fermented liquid (beer), and flavor is matured, the beer is filtered. In the packaging process, the beer is antiseptically filtered and is contained in barrels and/or bottles for distribution.

The quality of beer heavily depends on the quality control of the malting process, that is, the quality of produced malt. In general, a germinating process takes about four to six days. During germination, enzymes are synthesized, and starch and protein are partially degraded. The grade of malt degradation is referred to as "modification".

In the production process of beer, it is important to control the malt quality. Kohlbach Index, Hartong index at 45° C., diastatic power, viscosity, and β-glucan content are indexes that indicate the quality of malt. These parameters are controlled in the malting process to maintain constant malt quality.

The parameters for indicating malt modification are described below.

Kohlbach Index: the ratio of the nitrogen amount of congress wort prepared for analysis and the nitrogen amount of the whole malt. It indicates the extent of protein degradation in the malt. The higher the Kohlbach Index is, the more the malt is degraded. (modified).

Hartong index at 45° C.: the ratio of the extract of 45° C., 1-hour mashing of fine ground malt and the extract of the congress wort. The amount of extract mainly depends on the amount of starch and sugar. In malt, the degradation of protein components existing among starch particles affects the amount of extract. Accordingly, Hartong index at 45° C. indicates the degradation grade of both starch and protein. The higher the Hartong index at 45° C. is, the more the malt is modified.

Diastatic power: To determine the starch degradative enzyme power of malt, the amount of reduced sugar generated by affecting water-extraction liquid of malt to soluble starch is measured using iodometry. The starch degradative enzymes are synthesized as the barley germinates. In a brewing process, these enzymes are required for degradation of starch in malt and in adjuncts (for example corn starch). Malt with low diastatic power may cause a problem in a beer brewing process.

β-glucan content: β-glucan is the degradative product of cell wall of the malt. If the cell wall is not degraded enough, the lautering of mash becomes not smooth. Beer with high β-glucan content may cause haze after freezing.

The β-glucan content is measured as follows: after ground malt is heated in ethanol to inactivate enzyme, β-glucan in the malt is degraded to glucose by processing with lichenaze and β-glucosidase; and the amount of generated glucose is determined using glucoseoxidase/paroxidase method.

Viscosity: the viscosity of congress wort prepared for the analysis. Polysaccharides such as starch, dextrin, β-glucan, and pentosan mainly affect the viscosity of wort. The viscosity indicates the degree of degradation of stored starch and cell wall. The lower is the viscosity, the more the malt is moderated. The viscosity is measured at 20.00° C. with Ubbelohde type viscometer.

Friability: Friability is measured by a dedicated friability meter. Specifically, the friability is measured as follows. After being ground with a roller, malt samples are separated into one that passes through a specific slit and one that does not pass through the specific slit and remains. The separated malt samples are measured. The friability of the malt samples is defined as the ratio between the separated malt samples. Malt of which starch and cell wall are not well degraded is crystalline and consequently hard. Friability of such malt is low. Well degraded malt is mealy and easy to grind. The friability of such malt is high.

Conventionally, the above parameters for analyzing the modification of malt are determined with general analytical methods such as chemical analysis. However, the general analytical methods have problems such that the preparation and measurement of samples require considerable time. A rapid and simple analytical technique for malt quality evaluation is needed.

There are many analytical techniques for analyzing material, such as chemical analysis, optical analysis, and physical analysis (using X-ray, for example). Recently, electron spin resonance (ESR) analysis is drawing attention as an analytical technique to obtain molecular level information of material. The application of ESR analysis is being intensively studied.

The principle of ESR is exactly the same as that of nuclear magnetic resonance (NMR). ESR is a kind of magnetic resonance spectrum. Whereas the NMR measures the resonant absorption of nuclear spins, the ESR measures the resonant absorption of electron spins. The ESR most directly reveals information about the molecular structures and electron states of materials having unpaired electrons such as a radical and a transition metal complex (trivalent iron ion and bivalent copper ion, for example). As of now, the ESR is the most reliable analytical technique for detecting radicals.

ESR spectra show the following: g value indicating the position of resonance of the unpaired electrons, resonance intensity indicating the number of unpaired electrons, absorption width related to relaxation time, and hyper fine structure caused by the coupling between the unpaired electrons and atoms ($^1$H and $^{14}$N, for example) having nuclear spin near the unpaired electrons. Since each of radical species exhibits an intrinsic position of absorption, one can identify the radical species based on the g value. Additionally, one can consider reaction time and reaction mechanism based on the change over time of absorption (intensity).

The inventors intensely studied the application of ESR to the evaluation of state (quality) of malt in beer brewing. As a result of the study, the inventors discovered that, if an absorption intensity (signal intensity) is observed, the radical species is roughly identifiable based on the g value, and that there is a correlation between the absorption intensity (signal intensity) and the state (quality) of green malt and malt. The present invention, which is made based on the above discovery, provides a more rapid and simpler method of evaluating the quality of malt, than that of conventional analytical techniques.

SUMMARY OF THE INVENTION

The above problems can be solved by means of the present invention described below.

According to an aspect of the present invention, a quality evaluation method of green malt sampled in a germinating process of barley by electron spin resonance (ESR) spectrometry, includes the steps of: measuring a peak height of spectrum at a g value at which an unpaired electron derived from a carbon radical is resonant; determining an ESR signal intensity that is a ratio of the measured peak height of spectrum to a peak height of spectrum of a reference, per a unit weight of the sampled green malt; and evaluating a germination state of said sampled green malt by comparing the determined ESR signal intensity with a predetermined reference level.

The present invention makes it possible to determine the ESR signal intensity of green malt samples by using an electron spin resonance method, and to evaluate the quality of green malt samples based on the determined ESR signal intensity.

According to a second aspect of the present invention, a quality-evaluation method of malt sampled in a germinating process of barley by electron spin resonance (ESR) spectrometry, includes the steps of: measuring a peak height of spectrum at a g value at which an unpaired electron of a carbon radical is resonant; determining an ESR signal intensity that is a ratio of the measured peak height of spectrum to a peak height of spectrum of a reference, per a unit weight of the sampled malt; and evaluating a modification of the sampled malt by comparing the determined ESR signal intensity with a predetermined reference level.

The present invention makes it possible to obtain the ESR signal intensity of malt samples by using an electron spin resonance method, and to evaluate the quality of the malt samples based on the ESR signal intensity.

According to a third aspect of the present invention, an evaluation method of modification of malt sampled in a germination process of barley, includes the steps of: determining, in advance, a correlation between a parameter measured by general analytical methods including chemical analytical methods, said parameter indicating modification of the sampled malt, and an ESR signal intensity of the sampled malt, the ESR signal intensity being determined by an electron spin resonance spectrometry whereby a peak height of spectrum of said sampled malt is measured at a g value at which an unpaired electron of a carbon radical is resonant, and the ESR signal intensity is a ratio of the measured peak height of spectrum to a peak height of spectrum of a reference, per a unit weight of the sampled malt, and evaluating said modification of the sampled malt based on said parameters determined using the corresponding ESR signal intensity determined by said electron spin resonance spectrometry.

The present invention makes it possible to determine the ESR signal intensity of malt samples by using an electron spin resonance method, and to estimate parameters indicating the modification of malt based on the determined ESR signal intensity. Accordingly, the quality of malt can be evaluated.

At least one of a Kohlbach index, Hartong index at 45° C., diastatic power, β-glucan content, viscosity, and friability is used as the parameter for indicating the modification of malt.

BEST MODE FOR CARRYING OUT THE INVENTION

Embodiments of the present invention are described in more detail below. The outline of the ESR analyses performed by the inventors is described first.

(1) Barley, Malt Sample

If much moisture is contained in the sample, the moisture absorbs the electron spin resonance. When solid samples containing much moisture are measured with an ordinary ESR analysis method, the moisture needs to be removed. Accordingly, green malt was used after being lyophilized, as a sample for the analysis of germinating barleys (green malt). However, since malt contains low enough moisture, the malt was used as a sample without being lyophilized.

Japanese "Amagi Nijo" barleys and Canadian "Kendall" barleys were used as the samples. They were malted with a 90 kg-scaled pilot malting plant. The barleys were steeped in water at 14° C. and were germinated at 14° C. Malt with different germination time was prepared using an 8 kg-scaled kilning apparatus.

(2) ESR Analysis

The ESR analysis was carried out at the following measuring conditions.

Temperature of sample: room temperature

Sweep time: 60 seconds

Modulation width: 0.1 mT

Microwave power: 10.63 mW

Sweeps/measurement: 1 time

Internal standard: $Mn^{2+}$

Five whole grains of green malt and malt (0.4 g), or about 0.2 g of ground samples of them were put in an ESR sample tube (cylindrical tube), and their electron spin resonance absorption was measured with an electron spin resonance spectrometer. After the measurement of g value based on measured spectra, the signal intensity was calculated as the relative ratio of the peak height of the sample to the peak height of $Mn^{2+}$ used as the internal standard. The ESR signal intensity is defined as the relative height per a unit weight of sample (/g). One sample was measured 5 times and obtained data were averaged.

(3) ESR Preparatory Analysis of Green Malt and Malt

Figure 1:
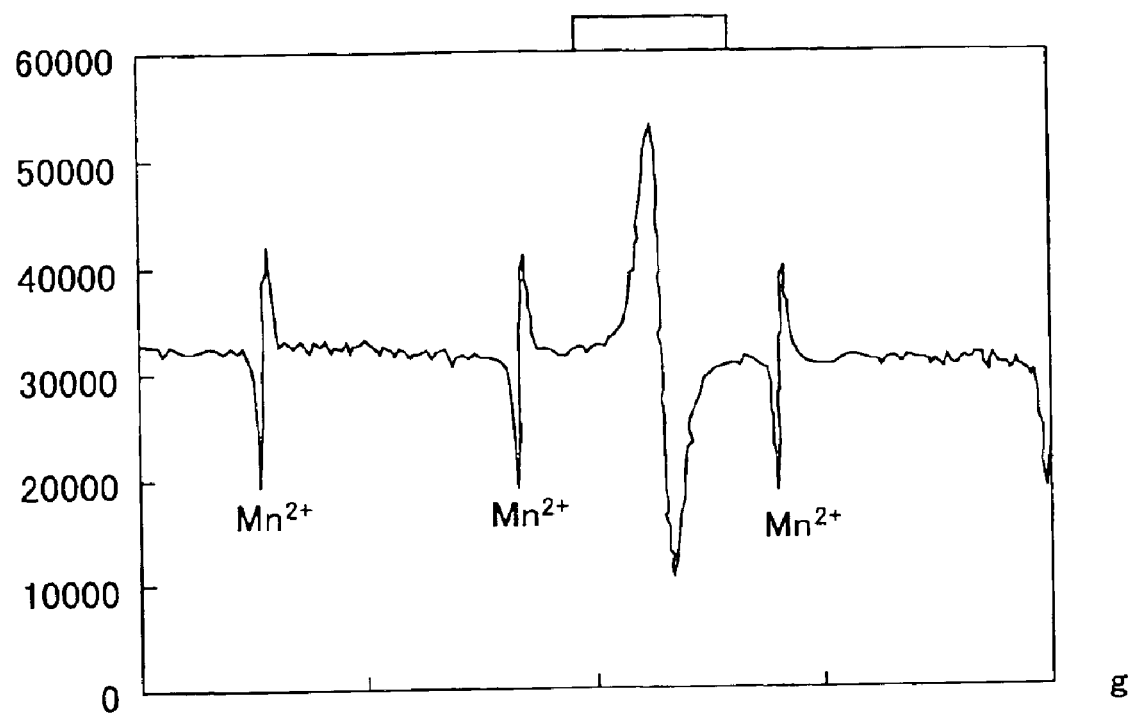
FIG. 1 is a graph showing an ESR spectrum of green malt.

FIG. 1 is a graph showing an ESR spectrum of ground green malt.

As is shown in FIG. 1, the spectrum shows a singlet peak at the position of g=2.0049. The g value g=2.0049 means that this spectrum is caused by carbon radicals. It is well known that, in food samples, which contain lipids and proteins (amino acid), for example, free radicals generated by the oxidation of lipids take hydrogen from the proteins and generate stable organic radicals derived from proteins, and that they produce a singlet peak around g=2.00. Accordingly, the inventors speculate that this peak is also caused by stable organic radicals derived from proteins in the green malt. In addition, ground malt samples and whole grain samples of malt and green malt (without grind) showed similar spectra pattern.

(4) Change in ESR Signal Intensity of Green Malt During Germination

Another experiment was performed to determine change in the ESR spectrum (signal intensity) of green malt during malting (germination).

Figure 2B:
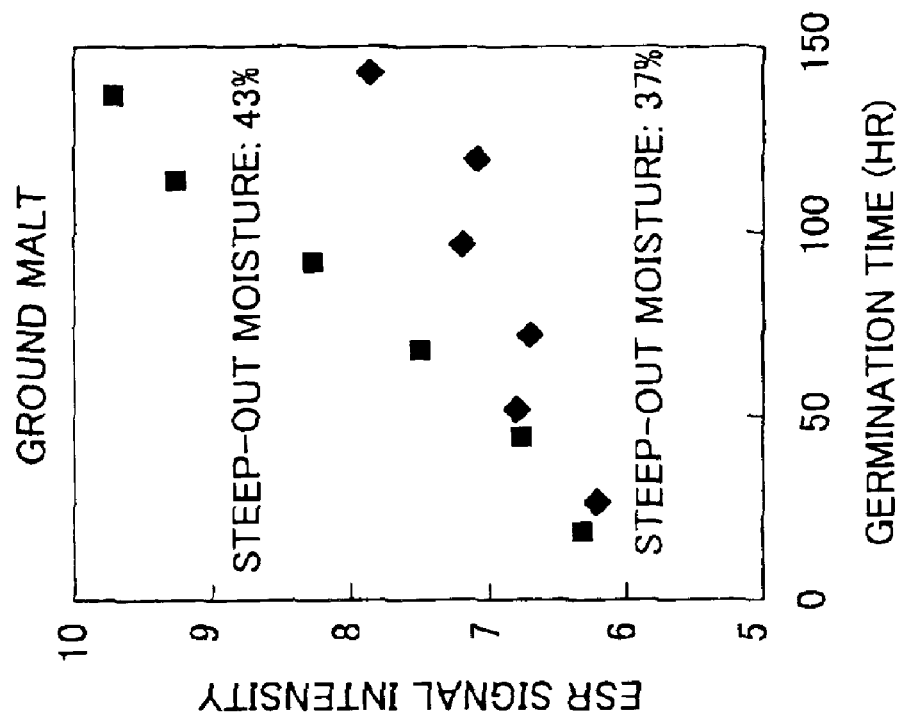
FIGS. 2A and 2B are charts showing the effect of steep-out moisture and germination time on the ESR signal intensity of green malt.
Figure 2A:
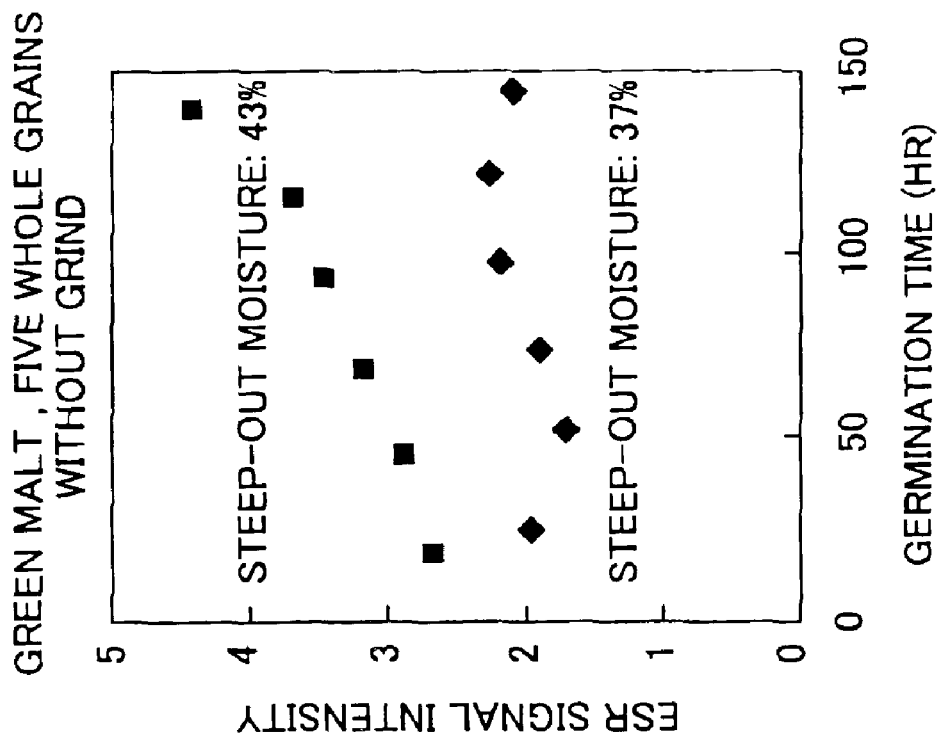

FIGS. 2A and 2B show the results of ESR measurement of the lyophilized green malt sampled once a day after germination and lyophilized. FIG. 2A shows the result of whole grains of green malt malted with two different steep-out moisture levels of 37% and 43%, and FIG. 2B shows the result of ground green malt malted with steep-out moisture levels of 37% and 43%.

These experimental results show that, as germination time passes, the ESR signal intensity increases. The results also show that the higher is the steep-out moisture level, the higher is the ESR signal intensity. Accordingly, it is found that the germination state of barley can be evaluated based on the ESR signal intensity.

From a comparison between the whole grain samples and ground samples, the ESR signal intensity of green malt increased with grind. This increase in ESR signal intensity could be derived from the increase in radicals by oxidation during grinding.

Based on the above experimental results, the inventors speculate that the amount of radicals is increased during germination because the germination activates the respiration of barley and consequently, the oxidation of ingredients contained in the barley, and accelerates the generation of stable organic radicals derived from proteins. Only the signal intensity changed with the germination time in the spectra. No new peak is observed in the spectra. The increase in stable organic radicals derived from proteins during germination is an interesting discovery in view of various changes of ingredients including the synthesis of enzyme in germinating barley. This discovery is expected to bring a new angle into the study of botanical germination.

(5) Relationship Between ESR Signal Intensity and Malt Parameters

Other green malts germinated for one through six days were kilned into malts and ground. The ESR signal intensities of the ground malts were compared.

Figure 3:
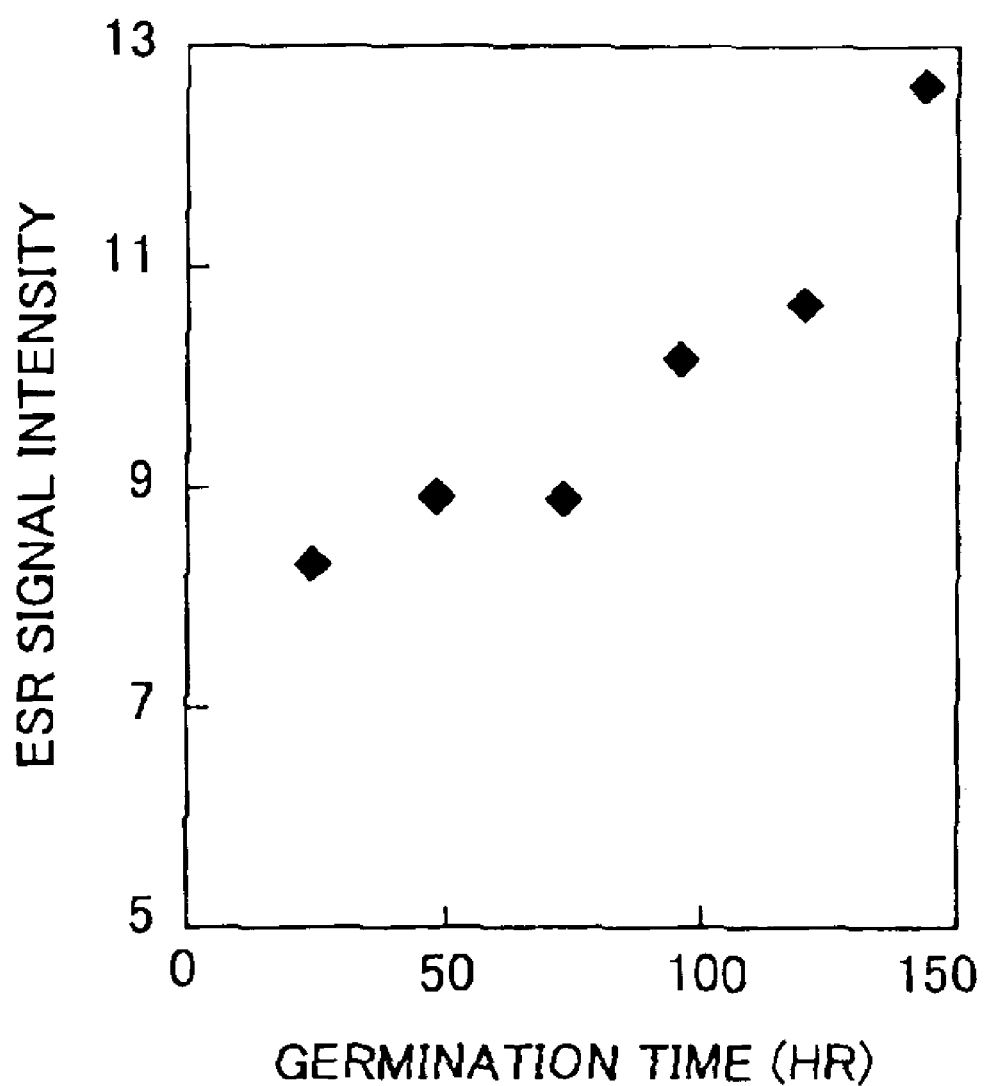
FIG. 3 is a chart showing the effect of germination time on the ESR signal intensity of malt.

FIG. 3 shows the result of the above experiment. As is shown in FIG. 3, the ESR signal intensity increased with germination time. Based on this result, the inventors confirmed that the increase in the ESR signal intensity of green malt with germination time is retained even after kilning.

The correlation between several typical parameters indicating malt modification and the ESR signal intensity was studied. FIGS. 4A through 4F show the relationship between the parameters indicating malt modification and the ESR signal intensity of malt samples used for the measurement shown in FIG. 3. FIGS. 4A through 4F show the relationship of malt quality parameters, that is, Hartong index at 45° C. (FIG. 4A), viscosity (FIG. 4B), β-glucan content (FIG. 4C), friability (FIG. 4D), diastatic power (FIG. 4E), and Kohlbach index (FIG. 4F), respectively, with the ESR signal intensity.

Figure 4A:
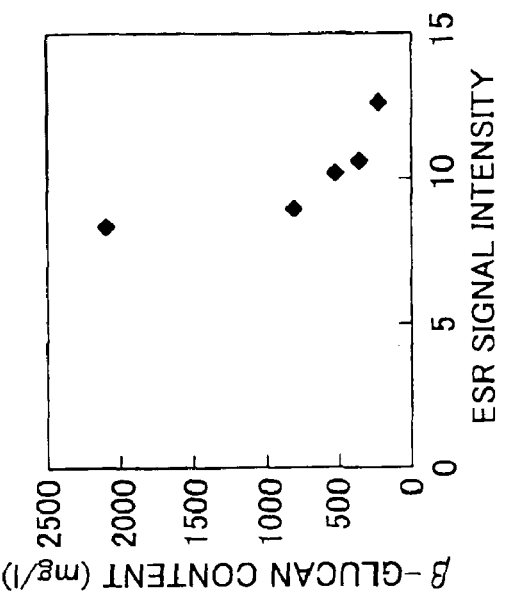
FIGS. 4A through 4F are charts showing the correlation between various parameters and the ESR signal intensity of malt.

FIG. 4A shows that Hartong index at 45° C. increases with signal intensity less than 9.5, and remains constant with signal intensity of 9.5 or more.

Figure 4B:
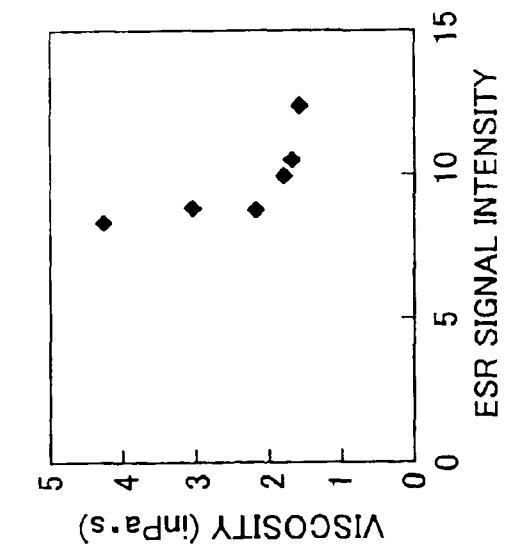

FIG. 4B shows that viscosity is constant with signal intensity of 12 or more.

Figure 4C:
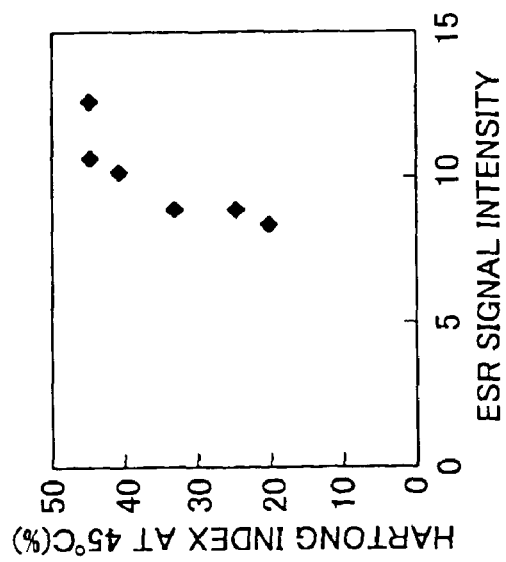

FIG. 4C shows β-glucan content does not remain constant over whole range of signal intensity.

Figure 4F:
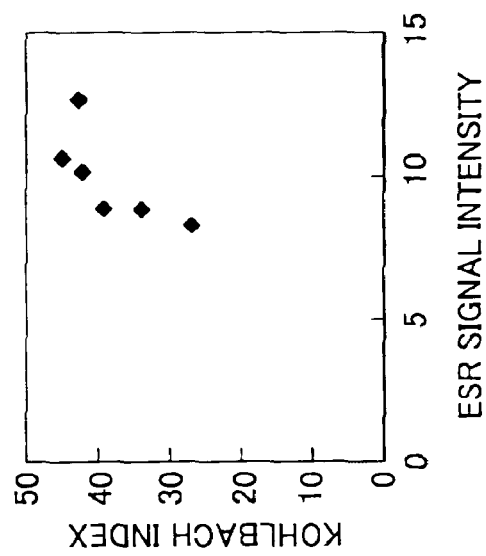
Figure 4E:
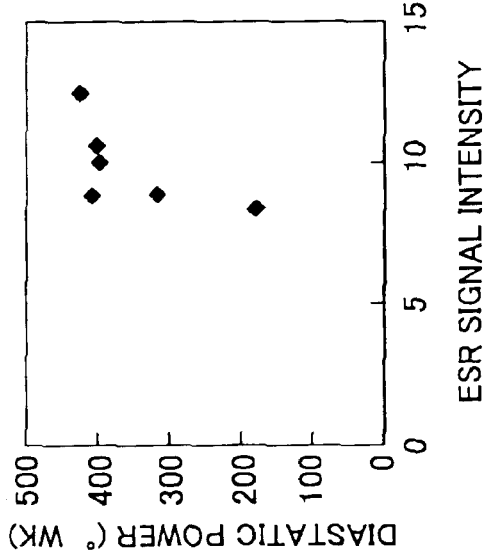
Figure 4D:
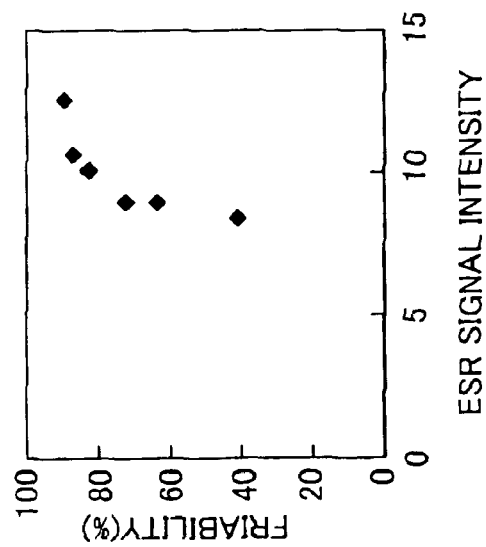

FIG. 4D shows that friability remains constant with signal intensity of 9 or more.

FIG. 4E shows that the diastatic power remains constant with signal intensity of 9 or more.

FIG. 4F shows that Kohlbach index remains constant with signal intensity of about 9 or more.

The results of the above experiments confirm that malt with ESR signal intensity between 9 and 15 is modified enough and satisfies the general requirement level of malt quality.

According to the above experimental results, germination state of malt can be estimated and evaluated based on the ESR signal intensity of the germinating malt (green malt).

The modification and/or diastatic power of malt can be evaluated by sampling green malt or malt during malting, and measuring ESR signal intensity using the ESR analysis. If the ESR signal intensity is equal to or more than a specific level, the malt quality can be guaranteed. Such a quality evaluation method can be used as a rapid and simple method to check the malt quality.

The ESR analysis of malt does not require lyophilizing the malt sample. The malt sample is ground and put in an ESR sample tube. The measurement by the ESR spectrometer takes less than two minutes. Although the setting of the ESR spectrometer takes about 30 minutes, the ESR analysis requires substantially less time than conventional method does. The preparation of malt samples is quite easy too.

Preferred embodiments of the present invention are described in detail above. However, the present invention is not limited to these embodiments, and variations and modifications may be made without departing from the scope of the present invention.

As is apparent from the above detailed description, the present invention makes it possible to evaluate the quality of green malt based on the ESR signal intensity of green malt sample using electron spin resonance method.

The present invention also makes it possible to evaluate the quality of malt based on the ESR signal intensity of malt sample using the electron spin resonance method.

Additionally, the present invention makes it possible to estimate parameters indicating malt modification such as Kohlbach index, Hartong index at 45° C., diastatic power, β-glucan content, viscosity, and friability based on parameters measured by the electron spin resonance method.

What is claimed is:

1. A quality evaluation method of green malt by electron spin resonance (ESR) spectrometry, comprising:

sampling green malt in a germination process of barley;

measuring a peak height of spectrum of the sampled green malt at a g value at which an unpaired electron derived from a carbon radical is resonant;

determining an ESR signal intensity that is a ratio of the measured peak height of spectrum to a peak height of spectrum of a reference, per a unit weight of the sampled green malt; and evaluating a germination state of the sampled green malt by comparing the determined ESR signal intensity with a predetermined reference level.

2. A quality evaluation method of malt by electron spin resonance (ESR) spectrometry, comprising:

sampling malt in a germination process of barley;

measuring a peak height of spectrum of the sampled malt at a g value at which an unpaired electron derived from a carbon radical is resonant;

determining an ESR signal intensity that is a ratio of the measured peak height of spectrum to a peak height of spectrum of a reference, per a unit weight of the sampled malt; and evaluating a modification state of the sampled malt by comparing the determined ESR signal intensity with a predetermined reference level.

3. An evaluation method of modification state of malt comprising:

determining a correlation between a parameter measured by general analytical methods including chemical analytical methods, said parameter indicating a modification state of the malt, and an ESR signal intensity of the sampled malt, the ESR signal intensity being determined by an electron spin resonance spectrometry whereby a peak height of spectrum of the malt is measured at a g value at which an unpaired electron of a carbon radical is resonant, and the ESR signal intensity is a ratio of the measured peak height of spectrum to a peak height of spectrum of a reference, per a unit weight of the malt;

sampling malt in a germination process of barley; and evaluating said modification of said sampled malt based on said parameters determined using the corresponding ESR signal intensity determined by said electron spin resonance spectrometry.

4. The evaluation method as claimed in claim 3, wherein said parameter is at least one of a Kohlbach index, Hartong index at 45°C., diastatic power, β-glucan content, viscosity, and friability.

* * * * *